(12) United States Patent
Zhang et al.

(10) Patent No.: US 11,980,364 B2
(45) Date of Patent: May 14, 2024

(54) ANVIL ASSEMBLY WITH CUTTING PLATE

(71) Applicant: Covidien LP, Mansfield, MA (US)

(72) Inventors: Xini Zhang, Shanghai (CN); Thomas R. Hessler, Bethel, CT (US)

(73) Assignee: COVIDIEN LP, Mansfield, MA (US)

( * ) Notice: Subject to any disclaimer, the term of this patent is extended or adjusted under 35 U.S.C. 154(b) by 99 days.

(21) Appl. No.: 17/796,782

(22) PCT Filed: Mar. 4, 2020

(86) PCT No.: PCT/CN2020/077684
§ 371 (c)(1),
(2) Date: Aug. 1, 2022

(87) PCT Pub. No.: WO2021/174431
PCT Pub. Date: Sep. 10, 2021

(65) Prior Publication Data
US 2023/0047701 A1 Feb. 16, 2023

(51) Int. Cl.
*A61B 17/072* (2006.01)
*A61B 17/32* (2006.01)

(52) U.S. Cl.
CPC .. *A61B 17/072* (2013.01); *A61B 2017/07221* (2013.01); *A61B 2017/320052* (2013.01)

(58) Field of Classification Search
CPC .................................................. A61B 17/072
See application file for complete search history.

(56) References Cited

U.S. PATENT DOCUMENTS

| | | | | |
|---|---|---|---|---|
| 4,415,112 A | * | 11/1983 | Green | A61B 17/072 227/19 |
| 6,988,650 B2 | * | 1/2006 | Schwemberger | A61B 17/072 227/176.1 |
| 7,147,140 B2 | * | 12/2006 | Wukusick | A61B 17/072 227/176.1 |
| 7,207,472 B2 | * | 4/2007 | Wukusick | A61B 17/072 227/181.1 |
| 2005/0139632 A1 | * | 6/2005 | Schwemberger | A61B 17/072 227/19 |
| 2005/0139634 A1 | * | 6/2005 | Schwemberger | A61B 17/072 227/19 |
| 2005/0139636 A1 | | 6/2005 | Schwemberger et al. | |

(Continued)

FOREIGN PATENT DOCUMENTS

| CN | 101433467 A | 5/2009 |
|---|---|---|
| CN | 105935302 A | 9/2016 |

(Continued)

OTHER PUBLICATIONS

International Search Report and Written Opinion dated Nov. 27, 2020, issued in corresponding international application No. PCT/CN2020/077684, 10 pages.

(Continued)

*Primary Examiner* — Nathaniel C Chukwurah
(74) *Attorney, Agent, or Firm* — Carter, DeLuca & Farrell, LLP

(57) ABSTRACT

A surgical stapling device (10) includes a replaceable cartridge assembly (44) having knife assembly (80) and an anvil assembly (42) including a cutting plate (52). The cutting plate (52) is configured be durable to maintain performance of the stapling device (10) over multiple firings.

20 Claims, 8 Drawing Sheets

(56) References Cited

U.S. PATENT DOCUMENTS

| | | | |
|---|---|---|---|
| 2017/0189012 A1* | 7/2017 | Adams | A61B 17/072 |
| 2017/0189022 A1* | 7/2017 | Adams | A61B 17/072 |
| 2019/0151011 A1 | 5/2019 | Brandt et al. | |

FOREIGN PATENT DOCUMENTS

| | | | |
|---|---|---|---|
| CN | 108472036 A | 8/2018 |
| CN | 208598459 U | 3/2019 |
| EP | 1090592 A1 | 4/2001 |
| EP | 2586380 A1 | 5/2013 |
| JP | 2003534089 A | 11/2003 |
| JP | 2016159154 A | 9/2016 |
| JP | 2019506204 A | 3/2019 |
| WO | 2014043971 A1 | 3/2014 |

OTHER PUBLICATIONS

European Search Report dated Nov. 9, 2023, issued in corresponding EP Appln. No. 20923492, 27 pages.
Japanese Office Action dated Dec. 1, 2023, issued in corresponding Japanese Appln. No. 2022552787, 4 pages.

* cited by examiner

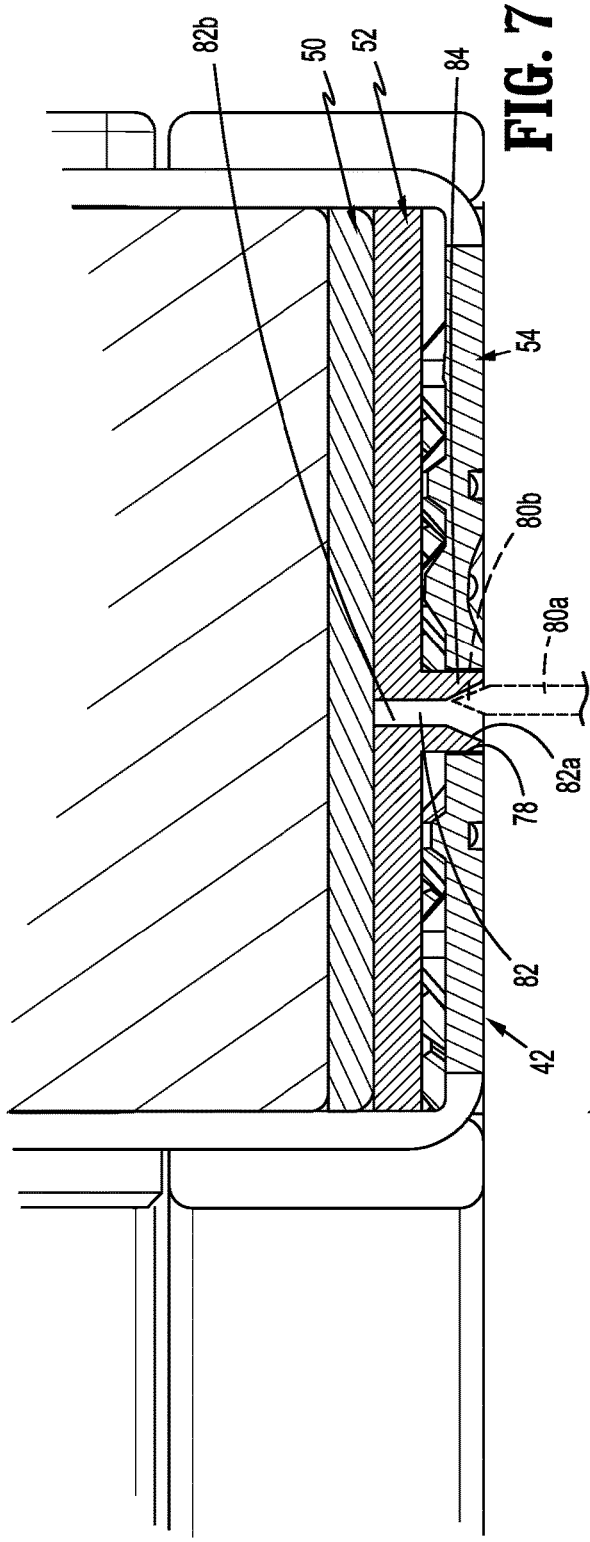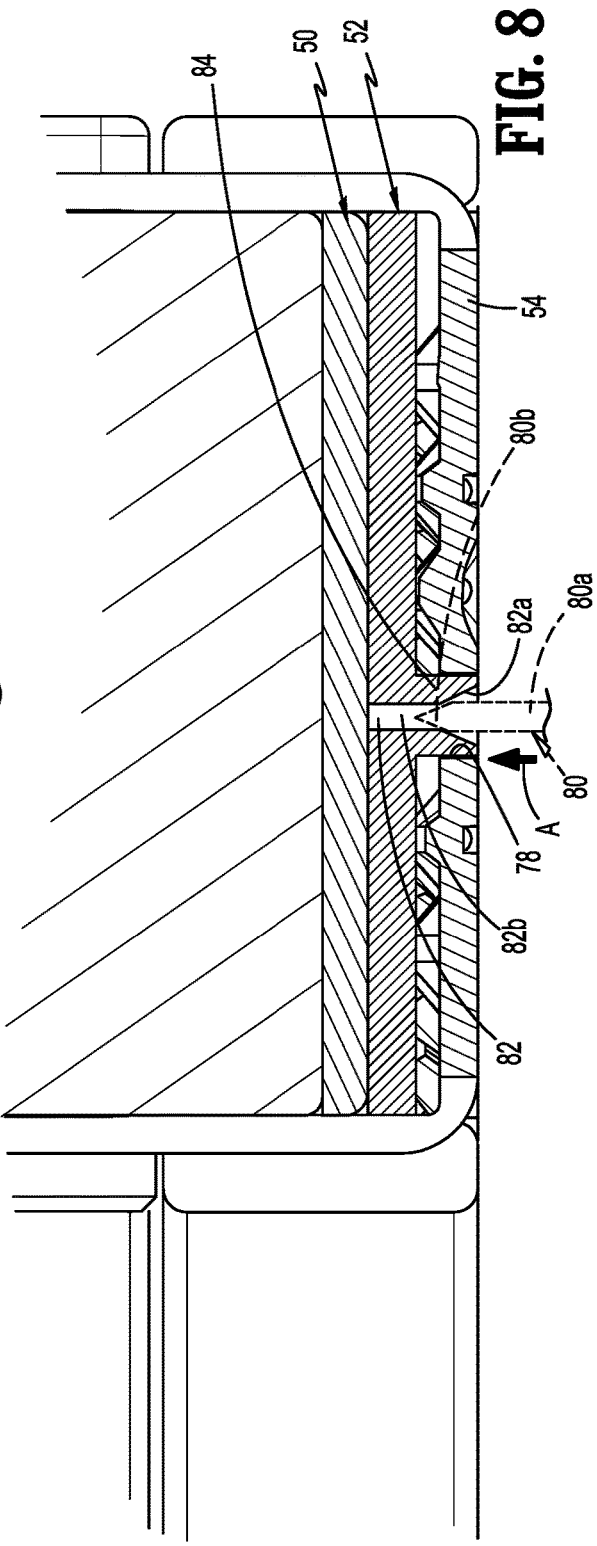

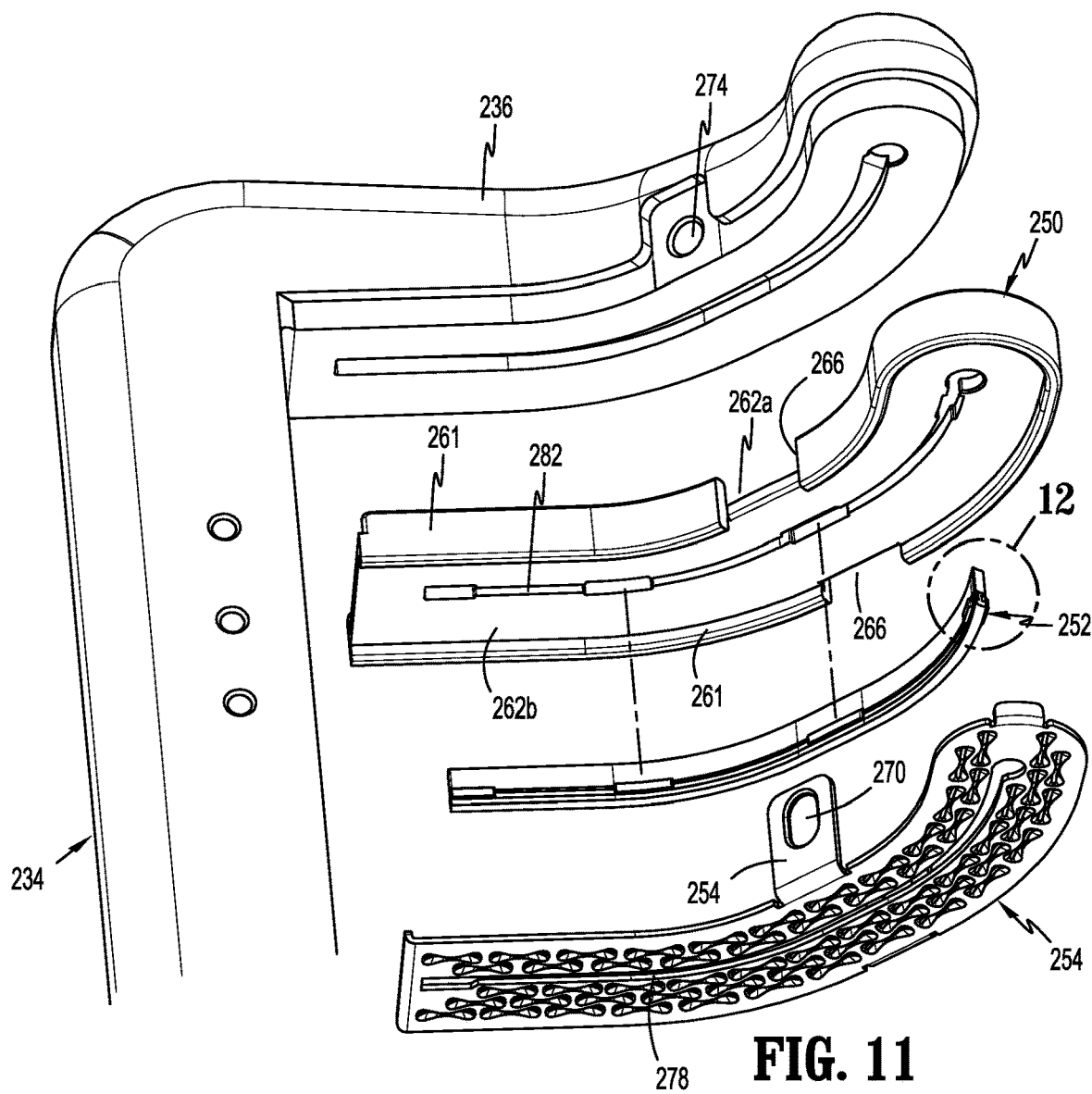
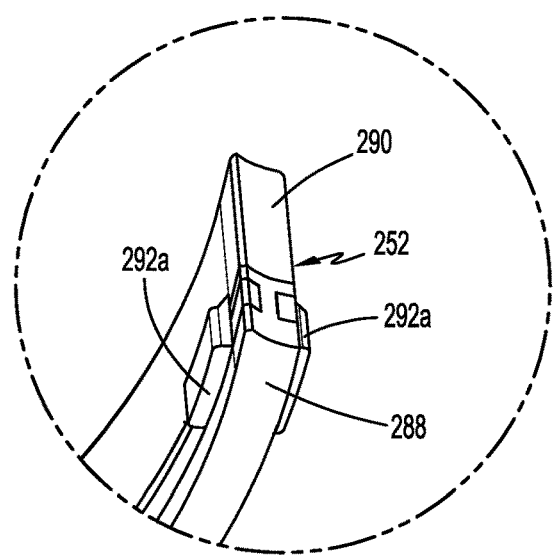
FIG. 11
FIG. 12

ANVIL ASSEMBLY WITH CUTTING PLATE

FIELD

The present technology is generally related to surgical stapling devices and, more particularly, to surgical stapling devices with removable staple cartridges.

BACKGROUND

Surgical stapling devices are commonly used during a variety of surgical procedures to expedite dissection and suturing of tissue and minimize trauma to a patient. Typically, these stapling devices include a cartridge assembly that includes a staple cartridge that can be replaced after each use of the stapling device to facilitate reuse of the stapling device. These devices also include a knife assembly for cutting tissue and an anvil assembly that supports a cutting plate which is engaged by the knife assembly to provide a more effective cutting process. The knife assembly includes a knife blade that has a sharpened cutting edge which is driven through tissue and into the cutting plate to transect or resect the tissue.

During a surgical procedure, the cutting plate may be damaged by the cutting edge of the knife blade. For example, the cutting edge of the knife blade may shave material off of the cutting plate or fracture the cutting plate. Although this may not be an issue with disposable devices, a damaged cutting plate may adversely affect the performance of a stapling device that is used multiple times.

A continuing need exists in the art for a reusable stapling device that can effectively cut tissue during multiple firings of the stapling device.

SUMMARY

Aspects of this disclosure are directed to a surgical stapling device including a replaceable cartridge assembly having knife assembly and an anvil assembly including a cutting plate. The cutting plate is configured to be durable to maintain performance over multiple firings of the stapling device.

One aspect of the disclosure is directed to a surgical stapling device including a handle assembly, a frame, a clamp slide assembly, and an anvil assembly. The frame defines a longitudinal axis and has a distal frame portion having a U-shaped configuration. The distal frame portion includes a first transverse portion, a second transverse frame portion, and a longitudinal portion interconnecting the first transverse portion and the second transverse portion. The first transverse portion is spaced from the second transverse portion to define a gap. The clamp slide assembly has a distal portion supported within the gap that is configured to receive a cartridge assembly. The anvil assembly is supported on the first transverse portion of the distal frame and includes an anvil filler, a cutting plate, and an anvil. The anvil filler is engaged with the first transverse portion, and the cutting plate is sandwiched between the anvil filler and the anvil. The anvil includes a proximally facing anvil forming surface and defines a first knife slot. The cutting plate includes a raised rib and defines a second knife slot formed in the raised rib. The second knife slot is aligned with the first knife slot, and the raised rib extends along the cutting plate and is received within the first knife slot. The second knife slot has a V-shaped inlet.

In aspects of the disclosure, the cutting plate is formed from a material selected from a polyether ether ketone, a polyoxymethylene, a polyphenylsulfone, or a metal, or combinations thereof.

In some aspects of the disclosure, the cutting plate is formed from a polyether ether ketone.

In certain aspects of the disclosure, the cutting plate is formed from metal using a metal injection molding process.

In aspects of the disclosure, the second knife slot includes a slot portion of uniform width that communicates with the V-shaped inlet, and the slot portion is positioned distally of the V-shaped inlet.

In some aspects of the disclosure, the stapling device includes a cartridge assembly having a cartridge body and a knife blade that is movable within the cartridge body from a retracted position to an advanced position.

In certain aspects of the disclosure, the knife blade has a body and a distal cutting edge.

In aspects of the disclosure, the body of the knife blade has a thickness that is greater than the width of the slot portion of the second knife slot.

In some aspects of the disclosure, the cutting plate and the anvil filler are integrally formed from a polyether ether ketone.

In certain aspects of the disclosure, the anvil assembly is curved along an axis transverse to the longitudinal axis.

Another aspect of the disclosure is directed to a surgical stapling device including a handle assembly, a frame, a clamp slide assembly, and an anvil assembly. The frame defines a longitudinal axis and has a distal frame portion that has a U-shaped configuration. The frame includes a first transverse portion, a second transverse portion, and a longitudinal portion interconnecting the first transverse portion and the second transverse portion. The first transverse portion is spaced from the second transverse portion to define a gap. The clamp slide assembly has a distal portion supported within the gap that is configured to receive and support a cartridge assembly. The anvil assembly is supported on the first transverse portion of the distal frame and includes an anvil filler, a cutting plate, and an anvil. The anvil filler is engaged with the first transverse portion of the distal frame portion and defines a first knife slot. The anvil is supported on the anvil filler and defines a second knife slot that is aligned with the first knife slot. The cutting plate includes an engagement member and a base member having a proximal portion and a distal portion. The engagement member is supported on the distal portion of the base member within the second knife slot. The base member formed of a compressible material and the engagement member formed of rigid material.

In aspects of the disclosure, the base member of the cutting plate is over molded onto the engagement portion of the cutting plate.

In some aspects of the disclosure, the base member is formed from rubber and the engagement portion is formed from a metal.

In certain aspects of the disclosure, the anvil filler includes detents formed along the first knife slot and the cutting plate includes tabs, wherein the tabs are received within the detents of the anvil filler to secure the cutting plate within the first knife slot of the anvil filler.

In aspects of the disclosure, the tabs are formed on the engagement portion of the cutting plate.

In some aspects of the disclosure, the engagement member includes a planar knife blade engagement surface.

In certain aspects of the disclosure, the first transverse portion defines an elongate channel and the base member is positioned within the elongate channel of the first transverse portion.

Other aspects of the disclosure are directed to an anvil assembly including an anvil filler, a cutting plate, and an anvil. The cutting plate is sandwiched between the anvil filler and the anvil. The anvil includes a proximally facing anvil forming surface and defines a first knife slot. The cutting plate includes a raised rib and defines a second knife slot formed in the raised rib. The second knife slot is aligned with the first knife slot, and the raised rib extends along the cutting plate and is received within the first knife slot. The second knife slot has a V-shaped inlet.

BRIEF DESCRIPTION OF THE DRAWINGS

Various aspects of the disclosure are described herein below with reference to the drawings, wherein:

FIG. 7 is a cross-sectional view taken along section line 7-7 of FIG. 5 illustrating a knife blade of a knife assembly as the knife blade engages the cutting plate of the anvil assembly;

FIG. 8 is a cross-sectional view taken along section line 7-7 of FIG. 5 illustrating a knife blade of a knife assembly with the knife blade engaged with the cutting plate of the anvil assembly;

FIG. 11 is a side perspective, exploded view of a distal portion of the surgical stapling device shown in FIG. 1 with an alternate version of the anvil assembly;

FIG. 12 is an enlarged view of the indicated area of detail shown in FIG. 11;

DETAILED DESCRIPTION

Figure 1:
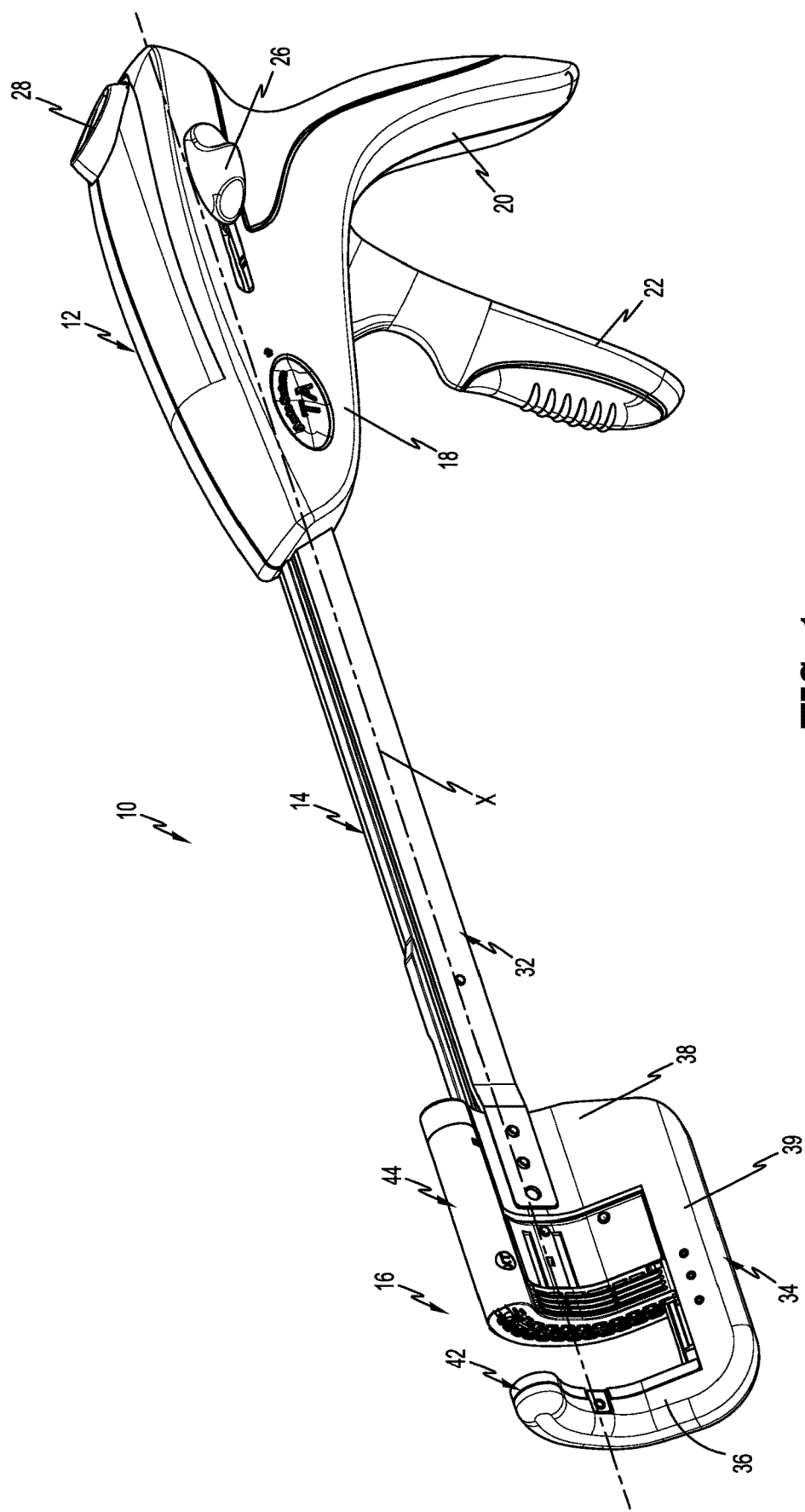
FIG. 1 is a side perspective view of a surgical stapling device including various aspects of the disclosure.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
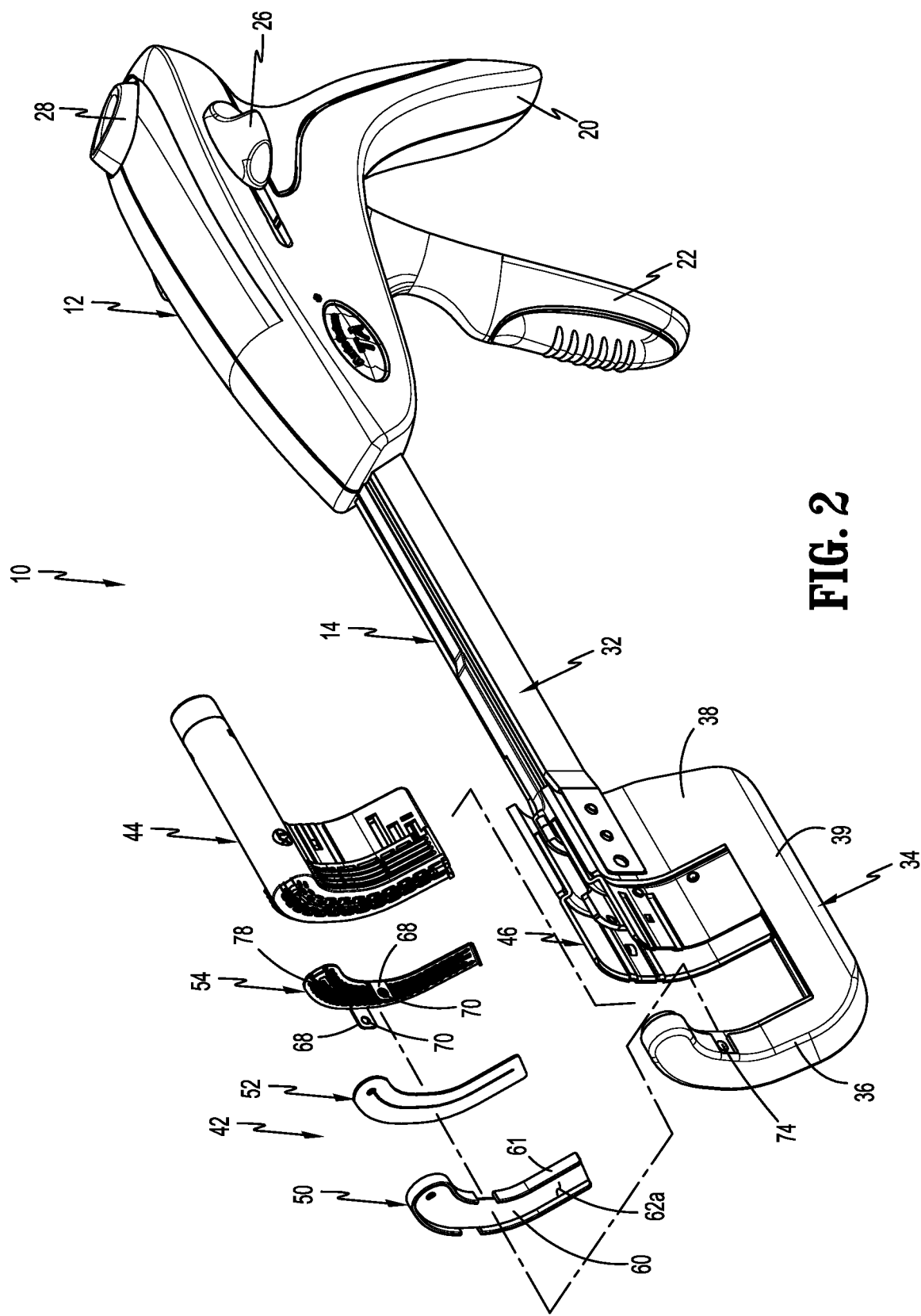
FIG. 2 is a side perspective view of the surgical stapling device shown in FIG. 1 with a cartridge assembly of the stapling device removed and the anvil assembly exploded.

FIGS. 1 and 2 illustrate the disclosed surgical stapling device shown generally as stapling device 10. The stapling device 10 includes a handle assembly 12, an elongate body 14 that extends distally from the handle assembly 12, and a tool assembly 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the movable trigger 22 is supported by the housing 18 to pivot towards the stationary handle 20 between non-actuated and actuated positions to operate the tool assembly 16. The handle assembly 12 also supports buttons 26 (only one is shown) positioned on each side of the housing 18 that are movable along the housing 18 to advance and retract an alignment pin pusher (not shown). The handle assembly 12 also includes a release button 28 that can be depressed to move the tool assembly 16 from a clamped position to an unclamped position. For a more detailed description of a suitable handle assembly 12, see, e.g., U.S. Pat. No. 6,817,508 ("the '508 patent").

The stapling device 10 includes a frame 32 that extends from the handle assembly 12 to the tool assembly 16. The frame 32 includes a distal frame portion 34 that has a U-shaped configuration. The distal frame portion 34 (FIG. 3) has a first transverse portion 36, a second transverse portion 38, and a longitudinal portion 39 that interconnects the first transverse portion 36 and the second transverse portion 38. The first and second transverse portions 36 and 38 are spaced from each other to define a gap 40 that extends between the first and second transverse portions 36 and 38. In some aspects of the disclosure, the first and second transverse portion 36 and 38 are curved along axes transverse to the longitudinal axis "X" of the elongate body 14 of the stapling device 10. Alternately, the first and second transverse portions may be linear or comprised of a plurality of linear portions that are positioned at angles in relation to each other.

The tool assembly 16 includes an anvil assembly 42 and a cartridge assembly 44. The cartridge assembly 44 is removably supported on a clamp slide assembly 46 and includes a staple cartridge 46 that supports a plurality of staples (not shown). The clamp slide assembly 46 (FIG. 2) includes a distal portion that is positioned in the gap 40 and is movable between retracted and advanced positions to move the cartridge assembly 44 in relation to the anvil assembly 42 through the gap 40 between an unclamped position (FIG. 1) located adjacent to the second transverse portion 38 and a clamped position located adjacent to the first transverse portion 36. For a detailed description of exemplary aspects of the operation and construction of a clamp slide assembly, see the '508 patent.

FIGS. 3-8 illustrate the anvil assembly 42 of the tool assembly 16 of the stapling device 10. The anvil assembly 42 is supported on the first transverse portion 36 of the distal frame portion 34 and includes an anvil filler 50, a cutting plate 52, and an anvil 54. The anvil filler 50, cutting plate 52, and the anvil 54 have configurations that correspond to the configuration of the first transverse portion 36 of the distal frame portion 34. The anvil filler 50 is fixedly secured to the first transverse portion 36 of the distal frame portion 34. In aspects of the disclosure, the anvil filler 50 includes a body portion 60 and a raised peripheral wall 61 that extends about the body portion 60 to define a distal recess 62a (FIG. 2) and a proximal recess 62b (FIG. 3) on the anvil filler 50. The distal recess 62a receives the first transverse portion 36 of the distal frame portion 34 to fixedly position the anvil filler 50 on the distal frame portion 34. The cutting plate 52 is received within the proximal recess 62b of the anvil filler 50 and the anvil 54 is positioned on top of the cutting plate 52 such that the cutting plate 52 is sandwiched between the anvil filler 50 and the anvil 54 within the proximal recess 62b of the anvil filler 50.

Figure 3:
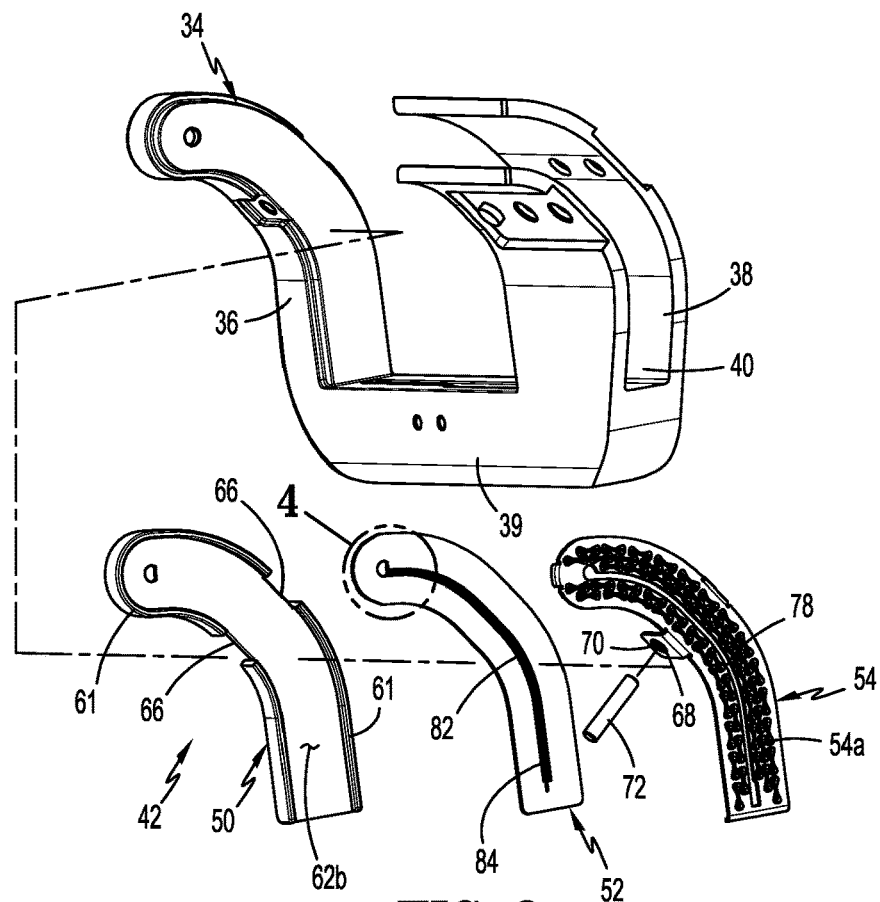
FIG. 3 is a side perspective exploded view of a distal portion of a frame of the surgical stapling device shown in FIG. 2 including the anvil assembly.
Figure 4:
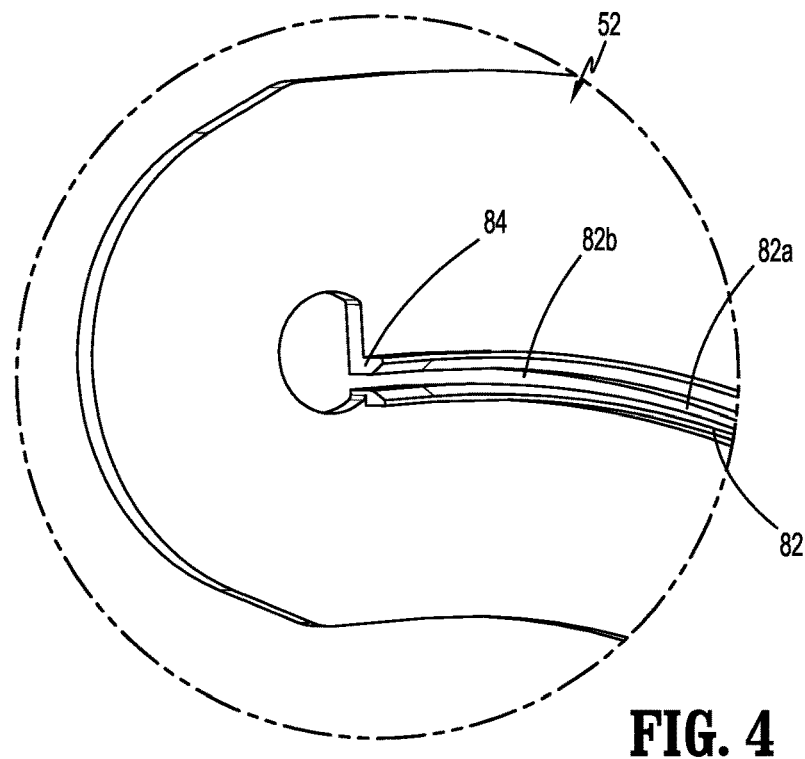
FIG. 4 is an enlarged view of the indicated area of detail shown in FIG. 3.
Figure 5:
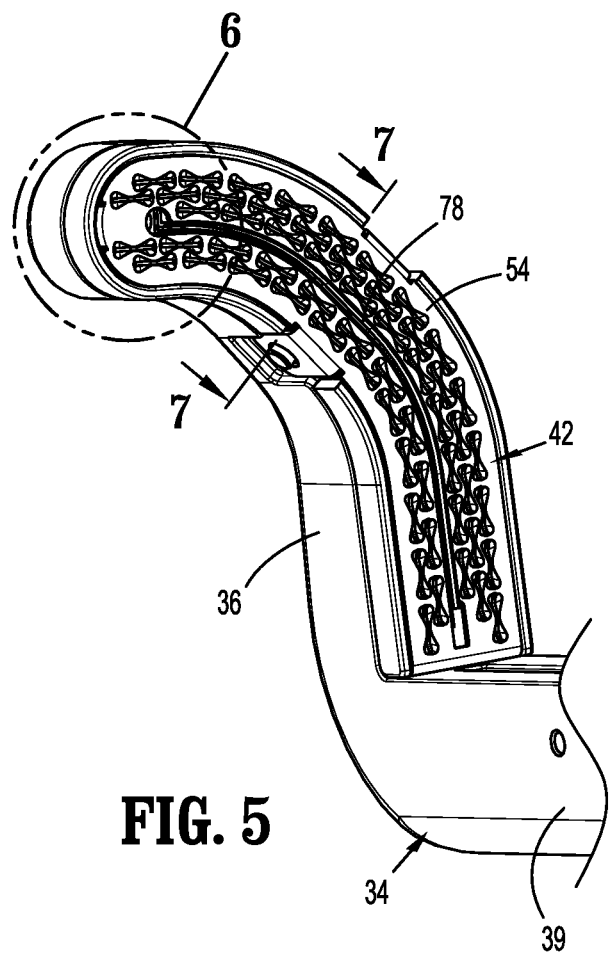
FIG. 5 is a perspective view from a proximal end of a distal portion of the surgical stapling device shown in FIG. 1 illustrating the anvil assembly the anvil assembly.
Figure 6:
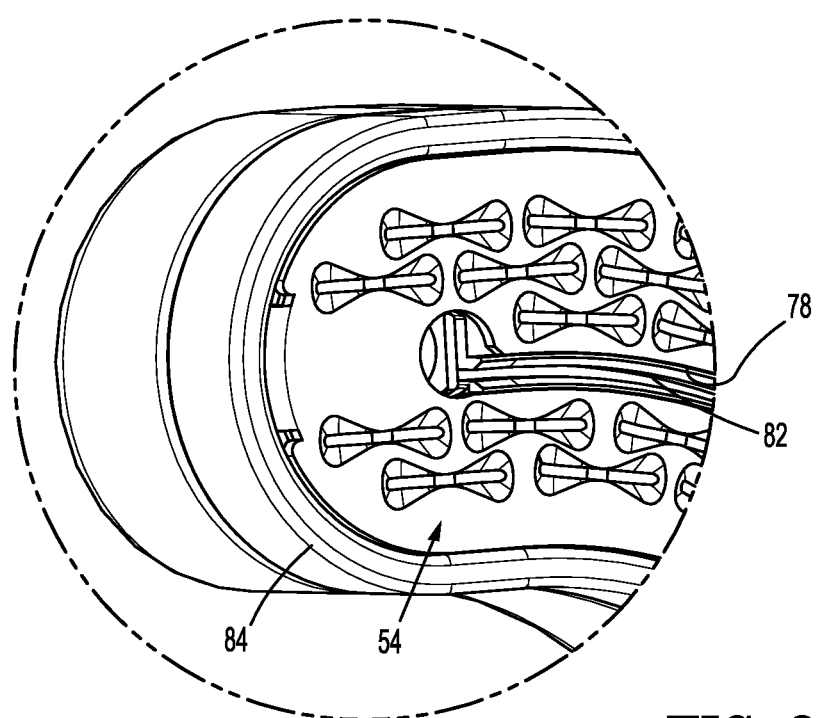
FIG. 6 is an enlarged view of the indicate area of detail shown in FIG. 5.

In aspects of the disclosure, the anvil filler 50 includes cutouts 66 that are positioned along the peripheral wall 61 of the anvil filler 50. The anvil 54 includes brackets 68 (FIG. 2) that extend distally from the anvil 54 through the cutouts 66. The brackets 68 each include a bore 70 that receive a screw or pin 72 (FIG. 3). The pin 72 extends through the bores 70 and into an opening 74 (FIG. 2) formed in the first transverse portion 36 of the distal frame portion 34 to secure the anvil 54, the anvil filler 50 and the cutting plate 52 to the distal frame portion 34.

The anvil 54 includes a proximally facing staple forming surface 54a (FIG. 3) and defines a knife slot 78 that extends through the anvil 54 and facilitates passage of a knife blade 80 (FIG. 8) of the cartridge assembly 44 through the anvil 54. The knife blade 80 includes a body 80a having a distally positioned cutting edge 80b. The cutting plate 52 also defines a knife slot 82 that is aligned with the knife slot 78 in the anvil 54. The knife slot 82 in the cutting plate 52 is formed in a raised rib 84 (FIG. 7) that extends from a proximally facing surface 86 of the cutting plate 52 proximally into the knife slot 78 of the anvil 54. The knife slot 82 includes a V-shaped inlet 82a and slot portion 82b of uniform width positioned distally of the V-shaped inlet 82a. In aspects of the disclosure, the slot portion 82b of the knife slot 82 has a width that corresponds to a thickness of the knife blade 80 (FIG. 8). In certain aspects, the width of the slot portion 82b of the knife slot 82 in the cutting plate 52 is about 80 nm less than the thickness of the body 80a of the knife blade 80 to ensure that tissue clamped between the staple cartridge 46 and the anvil 54 is cleanly cut. Other relative slot and knife blade dimensions are envisioned.

In aspects of the disclosure, the cutting plate 52 can be formed from a hard material such as a polyether ether ketone (PEEK) material, a polyoxymethylene (POM) material, or a polyphenylsulfone material (PPSU). Alternately, the cutting plate 52 can be formed of a metal such as stainless steel. In some aspects of the disclosure, the cutting plate 52 is formed using an injection molding process. For example, the cutting plate 52 can be formed using metal injection molding (MIM) process which provides an effective way of producing precision-shaped components. The hardness of the material used to from the cutting plate 52 minimizes any likelihood that the cutting plate 52 will be damaged during firing of the stapling device 10 (FIG. 1), e.g., that material will be shaved off of the cutting plate by the knife blade 80. The anvil filler can be formed of any suitable medical grade plastic although other materials of construction are envisioned.

FIGS. 7 and 8 illustrate the knife blade 80 of the cartridge assembly 44 (FIG. 2) as the stapling device 10 is fired and the knife blade 80 is advanced into the anvil assembly 42. As the knife blade 80 is advanced towards the anvil assembly 42 in the direction indicated by arrows "A", if the cutting edge 80a of the knife blade 80 is misaligned with the slot portion 82b of the knife slot 82 in the cutting plate 52 of the anvil assembly 42, the cutting edge 80b will engage the V-shaped inlet 82a of the knife slot 82 and be guided into the slot portion 82b.

Figure 10:
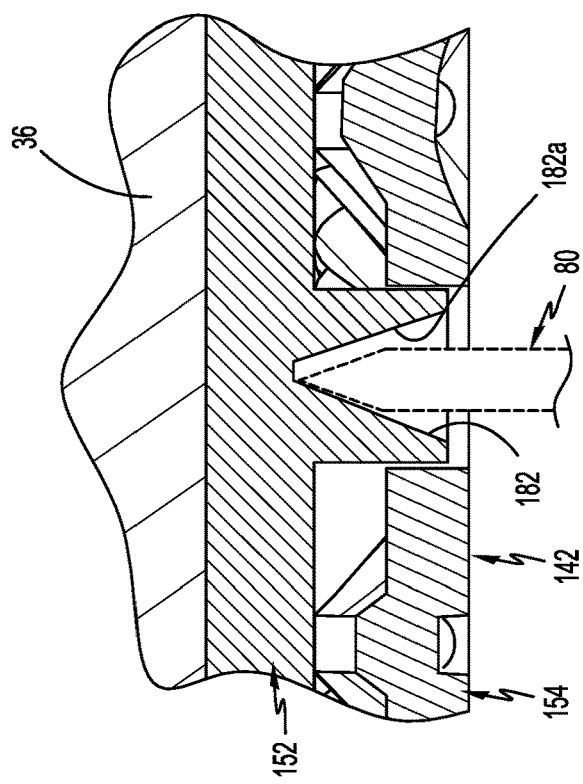
FIG. 10 is a cross-sectional view taken through an anvil assembly including the cutting plate shown in FIG. 9 illustrating a knife blade of a knife assembly with the knife blade engaged with the cutting plate of the anvil assembly.
Figure 9:
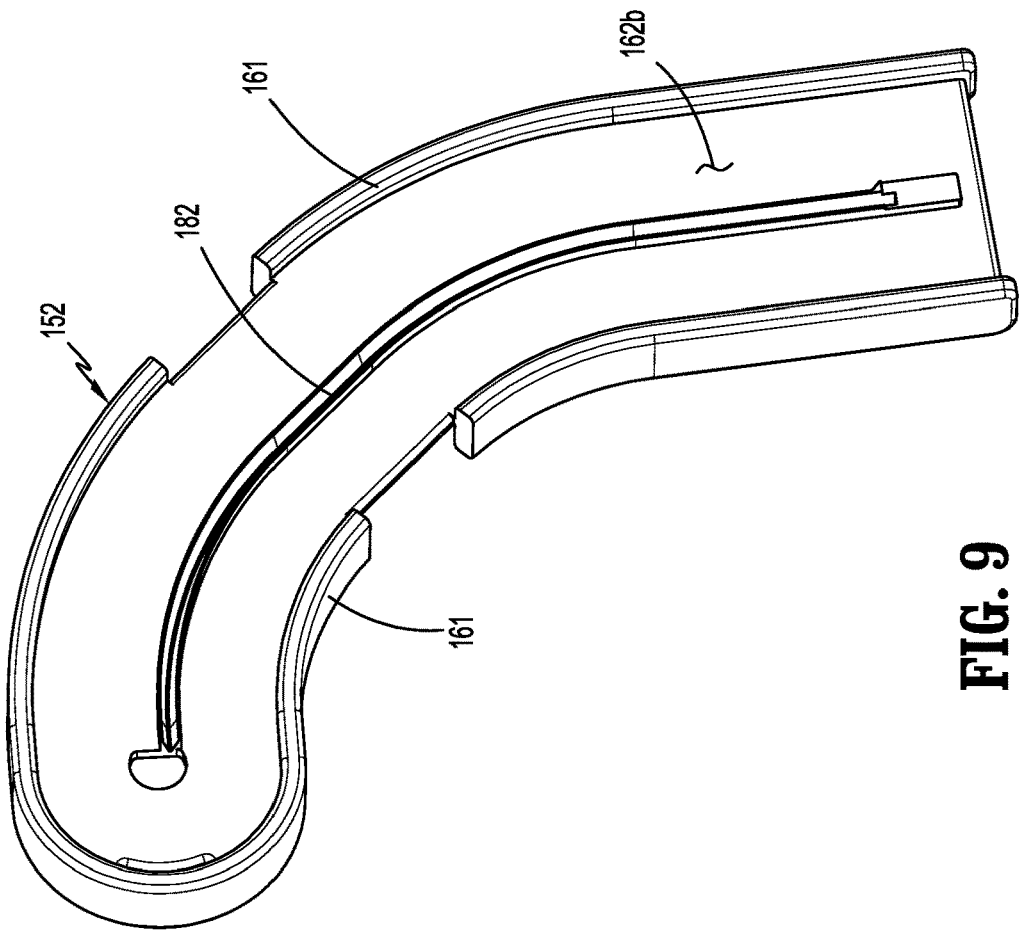
FIG. 9 is an alternate version of the cutting plate of the anvil assembly of the surgical stapling device shown in FIG. 1.
Figure 13:
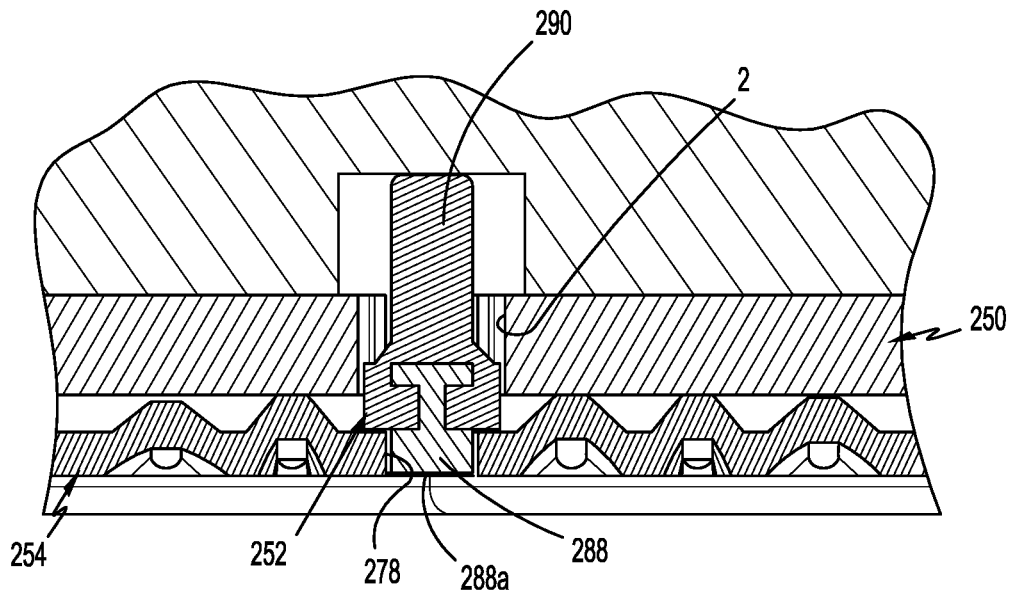
FIG. 13 is a cross-sectional view taken through the anvil assembly and the distal portion of the frame shown in FIG. 11.

FIGS. 9 and 10 illustrate an alternate version of the anvil assembly of the stapling device 10 (FIG. 10) shown generally as anvil assembly 142 (FIG. 10). The anvil assembly 142 is similar to the anvil assembly 42 (FIG. 3) except that the anvil filler 50 (FIG. 3) and the cutting plate 52 (FIG. 3) are formed as a single component shown generally as cutting plate 152. The cutting plate 152 is secured to the first transverse portion 36 of the distal frame portion 34 (FIG. 3) and the anvil 152 is received within the proximal recess 162b (FIG. 9) defined by the raised peripheral wall 161 of the cutting plate 152. The knife slot 182 of the cutting plate 152 is defined within the raised rib 184 of the cutting plate 152. As described above in regard to the cutting plate 152, the raised rib 184 extends proximally from the cutting plate 152 and into the knife slot 178 in the anvil 154. In aspects of the disclosure, the knife slot 182 in the cutting plate 152 defines a V-shaped blind bore 182a. Alternately, the knife slot 182 may have a configuration similar to knife slot 82 described above in regard to cutting plate 52 (FIG. 7).

In aspects of the disclosure, the cutting plate 152 also can be formed from a hard material such as a polyether ether ketone (PEEK) material, a polyoxymethylene (POM) material, or a polyphenylsulfone material (PPSU). Alternately, the cutting plate 152 can be formed of a metal such as stainless steel. In some aspects of the disclosure, the cutting plate 152 is formed using an injection molding process. For example, the cutting plate 152 can be formed using metal injection molding (MIM) process which provides an effective way of producing precision-shaped components. It is also envisioned that the cutting plate 152 can be formed of two components in which one of the components is over molded onto the second component. In this aspect of the disclosure, the portion of the cutting plate 152 to be engaged by the knife blade 80 should be formed of a hard material such as PEEK.

FIGS. 11-14 illustrate an alternate version of the disclosed anvil assembly shown generally as anvil assembly 242. The anvil assembly 242 includes an anvil filler 250, a cutting plate 252, and an anvil 254. The anvil filler 250 is similar to anvil 50 described above and includes a body portion 260 and a raised peripheral wall 261 that extends about the body portion 260 to define a distal recess 262a and a proximal recess 262b on the anvil filler 250. The distal recess 262a receives the first transverse portion 236 of the distal frame portion 234 to fixedly position the anvil filler 250 on the distal frame portion 234. The cutting plate 252 is received within the proximal recess 262b of the anvil filler 250 and the anvil 254 is positioned on top of the cutting plate 252 such that the cutting plate 252 is sandwiched between the anvil filler 250 and the anvil 254 within the proximal recess 262b of the anvil filler 250.

As described above in regard to anvil assembly 42 (FIG. 3), the anvil filler 250 includes cutouts 266 that are positioned along the peripheral wall 261 of the anvil filler 250. The anvil 254 includes brackets 268 (FIG. 11—only one is shown) that extend distally from the anvil 254 through the cutouts 266. The brackets 268 each include a bore 270 that receive a screw or pin, such as pin 72 (FIG. 3) that extends through the bores 270 and into an opening 274 (FIG. 11) formed in the first transverse portion 236 of the distal frame portion 234 to secure the anvil 254, the anvil filler 250 and the cutting plate 252 to the distal frame portion 34.

The anvil 254 defines a knife slot 278 that extends through the anvil 254 and facilitates passage of a knife blade 80 (FIG. 14) of the cartridge assembly 44 (FIG. 2) through the anvil 254. The knife blade 80 includes a body 80a having a distally positioned cutting edge 80b. The anvil filler 250 also defines a knife slot 282 that is aligned with the knife slot 278 in the anvil 254. The knife slot 282 in the anvil filler 282. The anvil filler 250 defines a plurality of detents 284 that are spaced along opposite sides of the knife slot 282.

The cutting plate 252 includes an engagement member 288 and a base member 290. The engagement member 288 is positioned on the distal portion of the base member 290 and is formed of a hard or rigid material such as a metal, e.g., stainless steel. The engagement member 288 includes an elongated body 292 that includes tabs 292a that are positioned along its length. The tabs 292a are received within the detents 284 of the knife slot 282 of the anvil filler 250 to secure the cutting plate 252 to the anvil filler 250. In aspects of the disclosure, the engagement member 288 includes a planar knife blade engaging surface 288a. The base member 290 of the cutting plate 252 is secured to the engagement member 288 and is formed of a compressible material, e.g., rubber. In aspects of the disclosure, the base member 290 is secured to the engagement member by over-molding. Alternately, other methods, materials, and/or techniques can be used to secure the engagement member 288 to the base member 290, e.g., adhesives, interlocking elements, etc.

The first transverse portion 236 of the distal frame portion 234 differs from the first transverse portion 36 of the distal frame portion 34 (FIG. 3) in that the first transverse portion 236 includes an elongated channel 294 that is aligned with the knife slot 282 of the cutting plate 252. When the anvil assembly 242 is assembled to the first transverse portion 236 of the distal frame portion 234, the base member 290 is positioned within the elongated channel 294 of the distal frame portion 236 such that the engagement member 288 is received within the knife slot 278 of the anvil 254. As described above, the engagement member 288 is secured to the anvil filler 250 within the knife slot 282.

Figure 14:
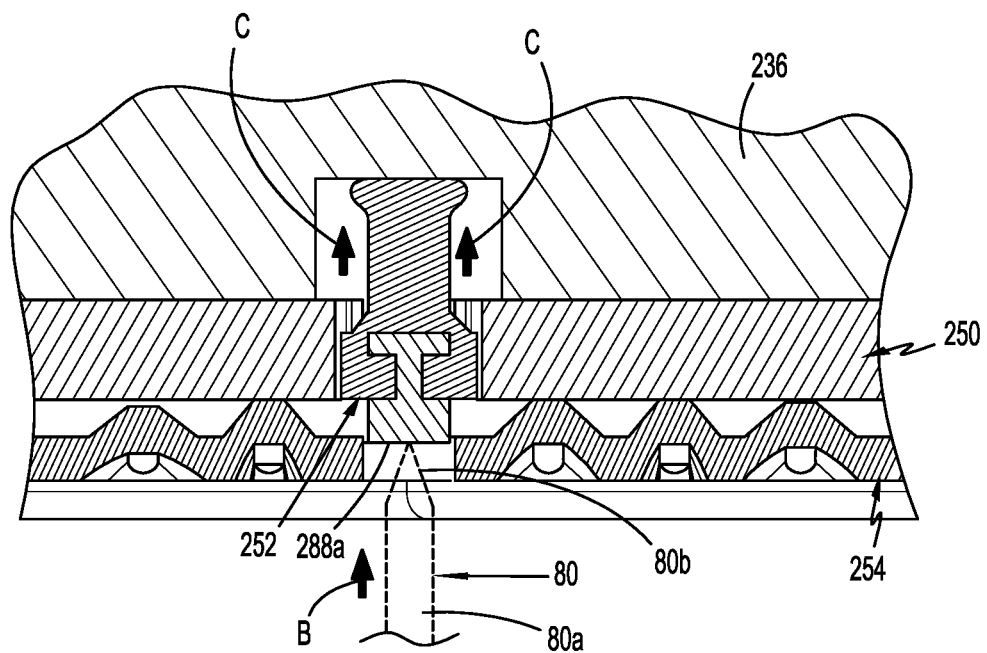
FIG. 14 is a cross-sectional view taken through the anvil assembly and the distal portion of the frame shown in FIG. 11 as a knife blade engages a cutting plate of the anvil assembly.

FIG. 14 illustrates the anvil assembly 242 as the cutting edge 80b of the knife blade 80 engages the engagement member 288 of the cutting plate 252 through the knife slot 278 of the anvil 254. When the knife blade 80 is advanced in the direction indicated by arrow "B" in FIG. 14 and the cutting edge 80b of the knife blade 80 engages the engagement member 288 of the cutting plate 252, the engagement member 288 is pushed distally to compress the base member 290 in the direction of arrows "C". The compressibility of the base member 290 is selected to provide sufficient resistance against movement of the engagement member 288 to allow the knife blade 80 to cut through tissue clamed between the staple cartridge 46 and the anvil 254.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A surgical stapling device comprising:
a handle assembly;
a frame defining a longitudinal axis and having a distal frame portion, the distal frame portion having a U-shaped configuration and including a first transverse portion, a second transverse portion, and a longitudinal portion interconnecting the first transverse portion and the second transverse portion, the first transverse portion being spaced from the second transverse portion to define a gap;
a clamp slide assembly having a distal portion supported within the gap, the distal portion of the clamp slide assembly configured to receive a cartridge assembly; and
an anvil assembly supported on the first transverse portion of the distal frame, the anvil assembly including an anvil filler, a cutting plate, and an anvil, the anvil filler engaged with the first transverse portion, and the cutting plate sandwiched between the anvil filler and the anvil, the anvil including a proximally facing anvil forming surface and defining a first knife slot, the cutting plate including a raised rib and defining a second knife slot formed in the raised rib, the second knife slot aligned with the first knife slot, the raised rib extending along the cutting plate and received within the first knife slot, wherein the second knife slot has a V-shaped inlet.

2. The surgical stapling device of claim 1, wherein the cutting plate is formed from a material selected from a polyether ether ketone, a polyoxymethylene, a polyphenylsulfone, or a metal, or combinations thereof.

3. The surgical stapling device of claim 2, wherein the cutting plate is formed from a polyether ether ketone.

4. The surgical stapling device of claim 2, wherein the cutting plate is formed from metal using a metal injection molding process.

5. The surgical stapling device of claim 1, wherein the second knife slot includes a slot portion of uniform width communicating with the V-shaped inlet, the slot portion positioned distally of the V-shaped inlet.

6. The surgical stapling device of claim 5, further including a cartridge assembly having a cartridge body and a knife blade, the knife blade being movable within the cartridge body from a retracted position to an advanced position and having a body and a distal cutting edge.

7. The surgical stapling device of claim 6, wherein the body of the knife blade has a thickness that is greater than the width of the slot portion of the second knife slot.

8. The surgical stapling device of claim 5, wherein the cutting plate and the anvil filler are integrally formed from a polyether ether ketone.

9. The surgical stapling device of claim 1, wherein the anvil assembly is curved along an axis transverse to the longitudinal axis.

10. A surgical stapling device comprising:
a handle assembly;
a frame defining a longitudinal axis and having a distal frame portion, the distal frame portion including having a U-shaped configuration and including a first transverse portion, a second transverse portion, and a longitudinal portion interconnecting the first transverse portion and the second transverse portion, the first transverse portion being spaced from the second transverse portion to define a gap;
a clamp slide assembly having a distal portion supported within the gap, the distal portion of the clamp slide assembly configured to receive and support a cartridge assembly;
an anvil assembly supported on the first transverse portion of the distal frame, the anvil assembly including an anvil filler, a cutting plate, and an anvil, the anvil filler engaged with the first transverse portion of the distal frame portion and defining a first knife slot, the anvil supported on the anvil filler and defining a second knife slot that is aligned with the first knife slot, the cutting plate including an engagement member and a base member, the base member having a proximal portion and a distal portion, the engagement member supported on the distal portion of the base member within the second knife slot, the base member formed of a compressible material and the engagement member formed of rigid material.

11. The surgical stapling device of claim 10, wherein the base member of the cutting plate is over molded onto the engagement portion of the cutting plate.

12. The surgical stapling device of claim 10, wherein the base member is formed from rubber and the engagement portion is formed from a metal.

13. The surgical stapling device of claim 10, wherein the anvil filler includes detents formed along the first knife slot and the cutting plate includes tabs, the tabs received within the detents of the anvil filler to secure the cutting plate within the first knife slot of the anvil filler.

14. The surgical stapling device of claim 13, wherein the tabs are formed on the engagement portion of the cutting plate.

15. The surgical stapling device of claim 10, wherein the engagement member includes a planar knife blade engagement surface.

16. The surgical stapling device of claim 10, wherein the first transverse portion defines an elongate channel and the base member is positioned within the elongate channel of the first transverse portion.

17. An anvil assembly comprising:
an anvil filler, a cutting plate, and an anvil, the cutting plate sandwiched between the anvil filler and the anvil, the anvil including a proximally facing anvil forming surface and defining a first knife slot, the cutting plate including a raised rib and defining a second knife slot formed in the raised rib, the second knife slot aligned with the first knife slot, and the raised rib extending along the cutting plate and received within the first knife slot, wherein the second knife slot has a V-shaped inlet.

18. The anvil assembly of claim 17, wherein the cutting plate is formed from a material selected from a polyether ether ketone, a polyoxymethylene, a polyphenylsulfone, or a metal, or combinations thereof.

19. The anvil assembly of claim 18, wherein the cutting plate is formed from a polyether ether ketone.

20. The anvil assembly of claim 18, wherein the cutting plate is formed from a metal using a metal injection molding process.

* * * * *